United States Patent
Takeuchi

(10) Patent No.: US 10,869,784 B2
(45) Date of Patent: Dec. 22, 2020

(54) METHOD FOR MANUFACTURING STRETCHABLE SHEET

(71) Applicant: Daio Paper Corporation, Ehime (JP)

(72) Inventor: Tomonari Takeuchi, Tochigi (JP)

(73) Assignee: Daio Paper Corporation, Ehime (JP)

( * ) Notice: Subject to any disclaimer, the term of this patent is extended or adjusted under 35 U.S.C. 154(b) by 80 days.

(21) Appl. No.: 16/324,287

(22) PCT Filed: Jul. 4, 2017

(86) PCT No.: PCT/JP2017/024416
§ 371 (c)(1),
(2) Date: Feb. 8, 2019

(87) PCT Pub. No.: WO2018/034069
PCT Pub. Date: Feb. 22, 2018

(65) Prior Publication Data
US 2019/0167487 A1 Jun. 6, 2019

(30) Foreign Application Priority Data
Aug. 19, 2016 (JP) .................................. 2016-161473

(51) Int. Cl.
*B32B 37/00* (2006.01)
*A61F 13/15* (2006.01)
(Continued)

(52) U.S. Cl.
CPC ...... *A61F 13/15593* (2013.01); *A61F 5/4404* (2013.01); *A61F 13/15* (2013.01);
(Continued)

(58) Field of Classification Search
USPC ....................................................... 156/73.1
See application file for complete search history.

(56) References Cited

U.S. PATENT DOCUMENTS

2002/0016122 A1  2/2002  Curro et al.
2014/0130956 A1  5/2014  Floberg et al.
(Continued)

FOREIGN PATENT DOCUMENTS

JP           4562391      8/2010
JP         2014-520589    8/2014
(Continued)

OTHER PUBLICATIONS

International Search Report, PCT/JP2017/024416, dated Oct. 3, 2017.
European Search Report for EP17841297, dated Feb. 28, 2020.

*Primary Examiner* — James D Sells
(74) *Attorney, Agent, or Firm* — Andrus Intellectual Property Law, LLP

(57) ABSTRACT

A stretchable elastic film is interposed in a stretched state between a first sheet layer having no elasticity and a second sheet layer having no elasticity. Heat melt energy is applied to a region of a large number of bonded portions spaced apart from each other by a heat melting apparatus from the outside of the first sheet layer and the second sheet layer to melt the elastic film. The first sheet layer and the second sheet layer are bonded directly or via an elastic film at the large number of bonded portions. The elastic film is caused to pass through the counter roll and the nip roll to pass along the counter roll and then pass along the anvil roll. The elastic film is stretched by making the circumferential speed of the anvil roll faster than the circumferential speed of the counter roll.

5 Claims, 18 Drawing Sheets

(51) Int. Cl.
*B29C 65/08* (2006.01)
*B32B 7/04* (2019.01)
*B32B 37/06* (2006.01)
*A61F 5/44* (2006.01)

(52) U.S. Cl.
CPC .. *A61F 13/15699* (2013.01); *A61F 13/15731* (2013.01); *B29C 65/08* (2013.01); *B32B 7/04* (2013.01); *B32B 37/06* (2013.01); *A61F 2013/15552* (2013.01); *A61F 2013/15869* (2013.01)

(56) References Cited

U.S. PATENT DOCUMENTS

| | | | |
|---|---|---|---|
| 2018/0008481 A1 | 1/2018 | Takahashi et al. | |
| 2018/0014984 A1 | 1/2018 | Sakai | |
| 2018/0015709 A1* | 1/2018 | Takeuchi | B29C 66/21 |
| 2018/0147094 A1* | 5/2018 | Takeuchi | A61F 13/513 |

FOREIGN PATENT DOCUMENTS

| | | |
|---|---|---|
| WO | 2016-121975 | 8/2016 |
| WO | 2016-121976 | 8/2016 |
| WO | 2016-121977 | 8/2016 |
| WO | 2016/121980 | 8/2016 |
| WO | 2016/121981 | 8/2016 |
| WO | 2016/121986 | 8/2016 |

\* cited by examiner

AREA RATE OF BONDED PORTIONS  STRETCHING STRESS
　　　　　A<B　　　　　　　　　　　A>B

AREA RATE OF BONDED PORTIONS
A<C=D

AFTER STRETCHING

STRETCHING STRESS
A>C=D

STRETCHABLE DIRECTION

DISTANCE BETWEEN NIP POSITION AND BONDING POSITION (mm)

MACHINE DIRECTION

MACHINE DIRECTION

METHOD FOR MANUFACTURING STRETCHABLE SHEET

CROSS-REFERENCE TO RELATED APPLICATIONS

This application is the U.S. national stage application of International Application PCT/JP2017/024416, filed Jul. 4, 2017, which international application was published on Feb. 22, 2018, as International Publication WO 2018/034069 in the Japanese language. The International Application claims priority of Japanese Patent Application No. 2016-161473, filed Aug. 19, 2016. The international application and Japanese application are both incorporated herein by reference, in entirety.

TECHNICAL FIELD

The present invention relates to a method for manufacturing a stretchable sheet including a first sheet layer and a second sheet layer sandwiching an elastic film.

BACKGROUND ART

In absorbent articles, for example, disposable diapers, in order to improve fit to the body surface, it is common to impart elasticity to appropriate positions such as around the legs and around the waist. Conventionally, as a technique for imparting elasticity, a technique of fixing an elongated elastic member such as a rubber thread in a state of being stretched in the longitudinal direction has been widely adopted, but when it is desired to impart elasticity with a certain width, a manner is adopted in which rubber threads are fixed along the width direction in a state of being arranged side by side at intervals.

On the other hand, as a material which imparts elasticity by pressing on a surface in place of a plurality of rubber threads disposed in parallel and which is selected also from consideration on texture, a stretchable sheet having a structure of nonwoven web/elastomer film/nonwoven web is proposed. (Refer to, for example, Patent Literature 1).

Patent Literature 1 discloses an un-apertured embodiment in which apertures are not formed in the whole of a first outer layer, a second outer layer, and an elastic film (elastomer) as well as an apertured embodiment in which apertures are formed through the whole of the first outer layer, the second outer layer, and the elastic film.

In the un-apertured embodiment, when the stretchable sheet is used as a sheet constituting, for example, the back side of a disposable diaper, there is a problem such as stuffiness because there is no air permeability.

On the other hand, in the apertured embodiment disclosed in Patent Literature 1, between the first outer layer and the second outer layer, an elastic film is supplied continuously; the elastic film is stretchable in a machine direction (MD) and has a melting point higher than the melting points of the first outer layer and the second outer layer or having no melting point; and the first outer layer and the second outer layer are directly bonded at predetermined sites by welding. Then, by applying a stretching force in a cross direction (CD), through holes that penetrate throughout the first outer layer, the elastic film, and the second outer layer are formed in the bond sites to ensure air permeability.

In any case, if an elastic film (elastomer) is stretched in the MD, so-called neck-in occurs by which the width of the elastic film is decreased. As a result of this neck-in, in order to obtain a laminated sheet having a desired width, it is necessary to prepare an elastic film having a width wider than each width of the first outer layer and the second outer layer, which leads to high cost of the material.

In addition, with respect to the CD of the actually laminated sheet, a stretching stress differs between the center in the width direction and the both side portions in the width direction due to the neck-in of the elastic film, and when the laminated stretchable sheet is applied to a product, for example, a disposable diaper, there may be a problem that uniform stretching stress cannot be obtained.

On the other hand, Patent Literature 2 discloses a method in which a plurality of stretch rolls is provided, and stretching is performed in the process of passing over the stretch rolls. In this method, "necking" is considered, and this method is intended to suppress "necking" (neck-in) by shortening the distance between the stretch rolls, but it does not seem to indicate sufficient effects.

CITATION LIST

Patent Literature

Patent Literature 1: JP 4562391 B2 (US 2002/0016122 A1)
Patent Literature 2: JP 2014-520589 A (US 2014/0130956 A1)

SUMMARY OF THE INVENTION

Technical Problem

Therefore, the main object of the present invention is to provide a method for manufacturing a stretchable sheet capable of suppressing neck-in.

Solution to Problem

The present invention that have solved the above problem will be described below.
(Basic Form)
A method for manufacturing a stretchable sheet of the present invention includes:
a supplying step in which a stretchable elastic film is interposed in a stretched state between a first sheet layer having no elasticity and a second sheet layer having no elasticity; and
a bonding step in which, in a state where the elastic film is interposed in a stretched state between the first sheet layer and the second sheet layer in the supplying step, the first sheet layer and the second sheet layer are bonded directly or via an elastic film at a large number of bonded portions by applying heat melt energy to a region of the large number of bonded portions spaced apart from each other by a heat melting apparatus from the outside of the first sheet layer and the second sheet layer to melt the elastic film,
wherein the heat melting apparatus has an anvil roll and an ultrasonic horn, the anvil roll has a large number of protrusions spaced apart from each other in a roll length direction and an outer circumference direction on an outer surface of the anvil roll,
a counter roll is disposed apart from the anvil roll,
a nip roll that nips the elastic film is disposed corresponding to the counter roll,
the elastic film passes through a nip position between the counter roll and the nip roll to pass along the counter roll and then pass along the anvil roll, the elastic film is stretched by making a circumferential speed of the anvil roll faster than a circumferential speed of the counter roll, and bonding is performed by the ultrasonic horn and a group of the protrusions of the anvil roll.

In the stretchable sheet obtained according to one embodiment of the present invention, no holes penetrating the first sheet layer and the second sheet layer are formed. It is different from the stretchable sheet illustrated in FIG. 5 or 7 of JP 4562391 B2 in this respect.

On the other hand, it is possible to form a through hole at least at a boundary portion between the elastic film and the bonded portion in the MD by supplying the elastic film in a stretched state in the MD to a bonding position. The reason why this through hole is formed will be described in detail later.

The heat melting apparatus has an anvil roll and an ultrasonic horn and is a unit for melting at least a part of at least one of the first sheet, the second sheet layer, and the elastic film by energy to be applied.

It is considered that, as the elastic film stretches, unevenness of a group of the protrusions on the anvil roll suppresses, as the resistance, the neck-in which is intended to cause due to the moving force toward the center in the width direction of the elastic film.

In the present invention, a counter roll is disposed apart from an anvil roll, and a nip roll that nips an elastic film is disposed corresponding to the counter roll.

The elastic film passes through the nip position between the counter roll and the nip roll and passes along the counter roll and the anvil roll, and by making the circumferential speed of the anvil roll faster than the circumferential speed of the counter roll, the elastic film is stretched.

That is, since the elastic film is nipped between the counter roll and the nip roll, by setting the circumferential speed of the anvil roll faster than the circumferential speed of the nip roll, the elastic film is substantially started to stretch (elongate) from the nip position.

Furthermore, since the elastic film passes along the anvil roll after passing along the counter roll, the resistance between the elastic film and the roll surface of the counter roll and the surface of the anvil roll suppresses the neck-in.

Moreover, owing to nipping, the resistance force between the elastic film and at least the surface of the counter roll further increases, which is considered to contribute to suppressing the neck-in.

It is desirable that the elastic film be not stretched on the upstream side of the nip position, and even if it is stretched, a stretch rate be equal to or less than 50% of the required stretch rate.

Therefore, according to a preferred embodiment of the present invention, stretching is started from the nip position. Alternatively, stretching of more than 50% of the required stretch rate is started from the nip position.

It is desirable that the distance between the nip position and the bonding position be less than 250 mm. Particularly 30 mm to 200 mm is desirable.

When the elastic film starts to separate from the anvil roll at a distance of 10 mm or less on the downstream side of the bonding position after passing the bonding position, it is desirable that a distance between the nip position and the position where the elastic film starts to separate from the anvil roll be less than 260 mm.

The anvil roll is desirably a crown roll rather than a flat roll. If the anvil roll is a crown roll, the resistance force of the elastic film to a crown roll surface is strengthened, which is considered to contribute to suppressing neck-in.

For example, the bonded portions are disposed in a staggered shape.

In one embodiment of the present invention, when the anvil roll is viewed in an unfolded state, it is desirable that an area rate of the total area occupied by the group of the protrusions included in the unit area be different at least according to the roll length direction.

On the other hand, it is possible to form a through hole at least at a boundary portion between the elastic film and the bonded portion in the MD by supplying the elastic film in a stretched state in the MD to the bonding position.

For the bonded portion of the present invention, for example, the following bonding modes can be raised.

(1) A mode in which the first sheet layer and the second sheet layer are partially melted and bonded to the elastic film, that is, the first sheet layer and the second sheet layer are bonded via the elastic film.

(2) A mode in which the elastic film melts and moves into the first sheet layer and into the second sheet layer, and the first sheet layer and the second sheet layer are bonded directly.

(3) An intermediate mode between the mode (1) and the mode (2), in which both surfaces of the elastic film melt and move into the first sheet layer and into the second sheet layer, but because the elastic film partially remains, the first sheet layer and the second sheet layer are bonded via the residual elastic film.

Among these modes, particularly in the mode (2) and the mode (3), difference in strength of the elastic film arises between a bonded portion and a non-bonded portion. Therefore, after releasing the stretched state of the stretchable sheet holding stretchability once to contract the stretchable sheet to make a product; or after bonding the stretchable sheet holding stretchability to another member and releasing the stretched state once to make a product, when the stretchable sheet is stretched in the stretchable direction mechanically or manually, breakage occurs at a boundary portion between the bonded portion and the non-bonded portion.

As a result, a through hole is formed.

With the through hole formed, there is an advantage that air permeability is secured. The through hole does not need to be formed at every bonded portion, and air permeability is shown even if the through holes are formed at not all but some bonded portions. When the elastic film is stretchable only in the MD, the through hole has a shape extending in the MD from the edge of the bonded portion. When the elastic film is stretchable both in the machine direction (MD) and in a direction orthogonal thereto (for example, CD), the through hole has a shape extending in both directions from the edge of the bonded portion, and may have an annular shape around the bonded portion.

As described above, since the elastic film of the present invention generally uses an elastomer, it is stretchable in the MD and the orthogonal direction (CD).

Besides a shape which does not have a directionality such as a circle, the bonded portion has a shape which has a length in the orthogonal direction (width direction: CD) being longer than the length in the MD.

To implement the method according to the present invention, the melting point of the elastic film is preferably about 80° C. to 145° C., and the melting points of the first sheet layer and the second sheet layer are preferably about 85° C. to 190° C., particularly preferably 130° C. to 190° C. The difference between the melting points of the first sheet layer and the second sheet layer and the melting point of the elastic film 30 that is a lower melting point is preferably about 50° C. to 80° C.

As a preferred specific example, the melting point of the elastic film is 95° C. to 125° C., the melting point of the first sheet layer is higher than 125° C. and not higher than 160° C., more preferably 130° C. to 160° C., and the second sheet layer has a melting point of higher than 125° C. and not higher than 160° C., more preferably 130° C. to 160° C.

When the anvil roll is viewed in an unfolded state, it is desirable that the area rate of the total area occupied by the group of the protrusions included in the unit area be different at least according to the roll length direction.

The protrusions correspond to the bonded portions. As a preferred example of the bonded portion, the area of the bonded portion is 0.14 mm$^2$ to 3.5 mm$^2$. Further, the area rate of the bonded portions is desirably 1.8% to 22.5%.

The area rate of the bonded portions in a stretchable region is 1.8% to 22.5%.

Here, "area rate" refers to a rate of a target portion to a unit area and expresses the rate as a percentage by dividing a total area of the target portions (for example, the bonded portions, the openings of the through holes) in a target region (for example, the stretchable region) by an area of the target region. In particular, the "area rate of the bonded portions" means an area rate in a state where the stretchable region is stretched to the elastic limit in the stretchable direction.

It is preferable that the area of the opening of the through hole in a state of natural length of the stretchable sheet is more than 1 time and not more than 1.5 times the area of the bonded portion.

The area of the opening of the through hole refers to a value while a stretchable structure is in a state of natural length and refers to the minimum value in the case where the area of the opening of the through hole is not uniform in the thickness direction such as a case where the area on the front surface of the elastic film is different from the area on the back surface of the elastic film.

By selecting the size, shape, separation distance, arrangement pattern in the roll length direction and roll circumferential direction, etc. of protrusions of the anvil roll to be described later, the area rate of the bonded portions described herein can be selected.

"Stretching stress" to be described later indicates "a stress (N/35 mm) in stretching to 50% of the elastic limit" measured by a tensile test at the initial chuck interval (distance between the gauge marks) of 50 mm, and the speed of testing of 300 mm/min according to JIS K7127: 1999 "Plastics—Determination of tensile properties—". When a test piece with a width of 35 mm cannot be cut out, a test piece is formed with a maximum possible width and the measured value is converted into a value at a width of 35 mm. Even if a sufficiently large test piece cannot be prepared from a target region with a small area, small test pieces can also be used for comparison of the stretching stress at least.

Further, in the embodiment to be described later, when a plurality of different stretching stresses are present in the region, how to collect a test piece for verifying the difference in the stretching stresses becomes a problem. In this case, in order to compare the stretching stresses, apart from obtaining the absolute value of the stretching stress, test pieces are taken from each site of the stretchable sheet, and for the respective test pieces, it is also possible to compare the stresses when the stretchable sheet is stretched from a natural length (100%) to 150% length.

Advantage Effects of Invention

As described above, the present invention provides a method for manufacturing a stretchable sheet capable of suppressing neck-in and reducing material costs.

BRIEF DESCRIPTION OF DRAWINGS

FIG. 13 is a graph showing results of experiment for generation of neck-in.

DESCRIPTION OF EMBODIMENTS

Hereinafter, embodiments of the present invention will be described in detail with reference to the accompanying drawings.

The stretchable sheet of the present invention can be used, for example, for absorbent articles that absorb and retain body fluids, such as disposable diapers, sanitary napkins, absorbent pads and the like.

As illustrated in FIGS. 5 to 8, in the stretchable sheet, an elastic film 30 stretchable in the front-back direction is stacked between a first sheet layer 21 made of, for example, a nonwoven fabric having no elasticity and a second sheet layer 22 having no elasticity such as a nonwoven fabric, and the first sheet layer 21 and the second sheet layer 22 are bonded to each other directly or via the elastic film 30 with a large number of bonded portions 40 spaced apart from each other.

Here, the expression "no elasticity" does not mean that the first sheet layer 21 and the second sheet layer 22 do not stretch at all. Instead, it means that the elastic film is not substantially stretchable compared with the elastic film.

Figure 9:
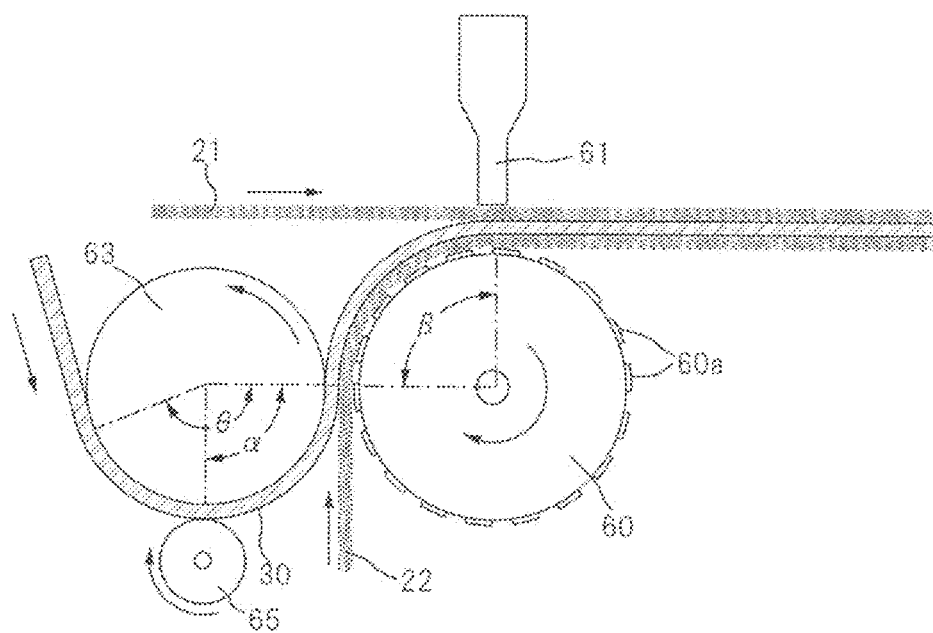
FIG. 9 is a schematic diagram of a first bonding example according to the present invention.

Regarding bonding, for example, as illustrated in FIG. 9 indicating a first bonding example according to the present invention, between an anvil roll 60 having protrusions 60a formed in a predetermined pattern on the outer surface and an ultrasonic horn 61, the first sheet layer 21, the elastic film 30, and the second sheet layer 22 are supplied, ultrasonic melting energy is applied by the ultrasonic horn 61, and, for example, mainly the elastic film 30 is melted, to bond the first sheet layer 21 and the second sheet layer 22.

A counter roll 63 is disposed so as to face the anvil roll 60. Further, a nip roll 65 for nipping the elastic film 30 is provided on the counter roll 63. The anvil roll 60 is driven such that the circumferential speed of the anvil roll 60 becomes faster than the circumferential speed of the counter roll 63 and the nip roll 65.

In this structure of the apparatus, after the elastic film 30 passes through a nip position at which the elastic film 30 is nipped by the counter roll 63 and the nip roll 65, the elastic film 30 passes along the outer periphery of the counter roll 63 and then passes along the anvil roll 60.

At that time, the elastic film 30 is stretched by setting the circumferential speed of the anvil roll 60 to be driven to be faster than the circumferential speed of the counter roll 63 and the nip roll 65, and bonding is performed by the ultrasonic horn 61 and the group of the protrusions 60a of the anvil roll 60.

At this time, by selecting the speed difference that makes the circumferential speed of the anvil roll 60 faster than the circumferential speed of the nip roll 63, the stretch rate in the manufacturing process of the elastic film 30 (when the length in a natural state is taken as 100%) can be set.

In the example of FIG. 9, although the anvil roll 60 and the counter roll 63 do not nip the elastic film 30, they are disposed close to each other. Then, the elastic film 30 passes along the counter roll 63 with the holding angle θ of more than 90° and less than 180° with respect to the counter roll 63. From the nip position with the nip roll 65, the holding angle α is approximately 90°.

The elastic film 30 and the second sheet layer 22 pass along the anvil roll 60 with a holding angle β of about 90°.

Figure 10:
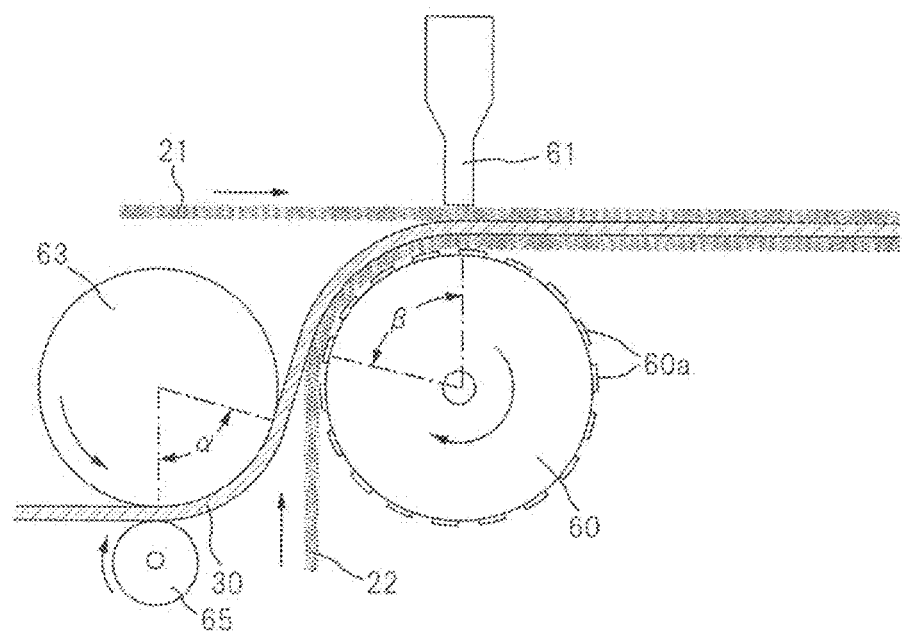
FIG. 10 is a schematic diagram of a second bonding example according to the present invention.

The arrangement of the anvil roll 60, the counter roll 63, and the nip roll 65 can be selected as appropriate. For example, as illustrated in FIG. 10 indicating a second bonding example, the anvil roll 60 and the counter roll 63 are disposed slightly apart without nipping the elastic film 30. In the example of FIG. 10, the elastic film 30 is not in contact with the counter roll 63 until reaching a position of the nip roll 65.

As a result, the elastic film 30 passes along the counter roll 63 with the holding angle α of less than 90° with respect to the counter roll 63.

The elastic film 30 and the second sheet layer 22 pass along the anvil roll 60 with the holding angle β of less than 90°.

A distance from a position where the elastic film 30 is separated from the counter roll 63 to a position where the elastic film starts to be held by the anvil roll 60 is 50 mm or less, preferably 10 mm or less, particularly preferably 5 mm or less for suppressing neck-in.

Figure 11:
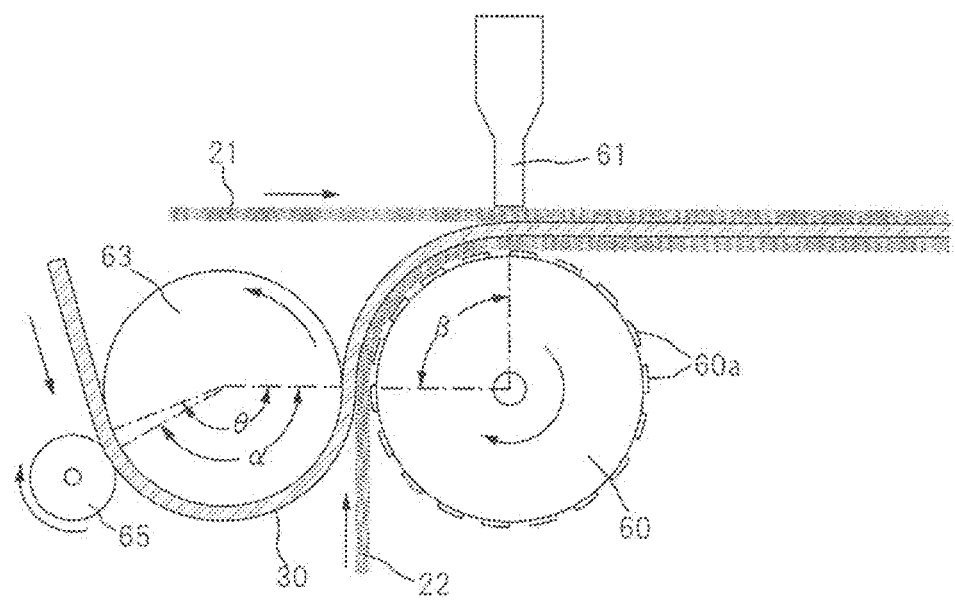
FIG. 11 is a schematic diagram of a third bonding example according to the present invention.

In the example of FIG. 11 indicating a third bonding example, although the anvil roll 60 and the counter roll 63 do not nip the elastic film 30, they are disposed close to each other. Then, the nip roll 65 is disposed to the counter roll 63, and the elastic film 30 passes along the counter roll 63 with the holding angle α of more than 90° and less than 180°.

In the first bonding example to the third bonding example described above, stretching (elongation) of the elastic film 30 is started from the nip position between the counter roll 63 and the nip roll 65. However, in the fourth bonding example 12, the elastic film 30 is nipped between the pre-roll 62 and the pre-nip roll 64, and the elastic film 30 is nipped between the counter roll 63 and the nip roll 65, such that the circumferential speed of the pre-roll 62 and the pre-nip roll 64, the circumferential speed of the counter roll 63 and the nip roll 65, and the circumferential speed of the anvil roll 60 are gradually increased, whereby it is possible to stretch (elongate) two stages.

It is possible to stretch (elongate) three stages by adding the same structure.

Figure 13:
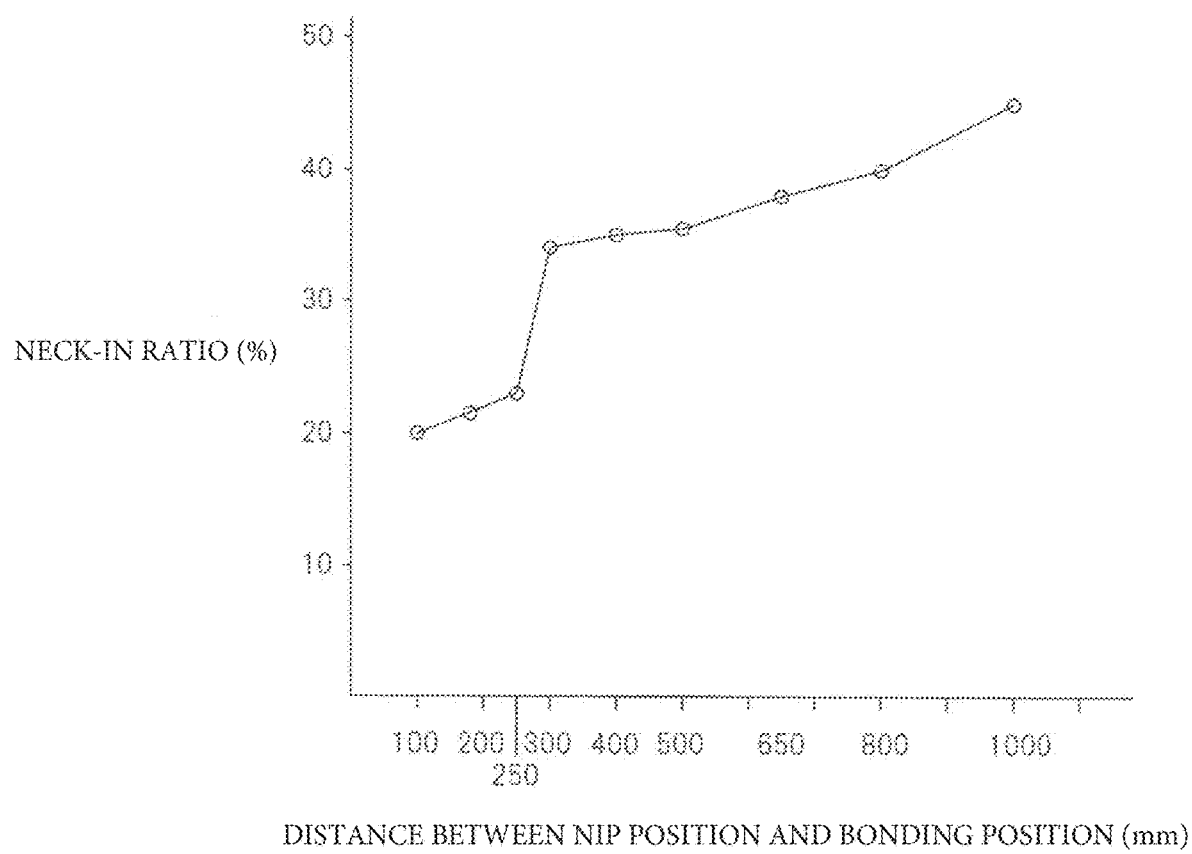

FIG. 13 shows a result of examining the relationship between the distance from the nip position to the bonding position and the neck-in ratio.

According to FIG. 13, the neck-in ratio does not increase in direct proportion to the distance between the stretching rollers, but the neck-in ratio suddenly increases when the distance between the stretching rollers is reached to 250 mm or more. Therefore, in the example illustrated in FIG. 9, it is desirable that the distance from the nip position for the elastic film 30 between the counter roll 63 and the nip roll 65 to the bonding position of the anvil roll 60 be 250 mm or less. In particular, 180 mm or less is desirable.

Further, with respect to the counter roll 63, the holding angle α from the nip position for the elastic film 30 to the position where the elastic film 30 is separated is desirably 300° to 30° (more desirably 120° to 45°) to suppress neck-in. It is desirable for the neck-in suppression that the holding angle β of the anvil roll 60 is 270° to 30° (more desirably 120° to 45°).

Figure 12:
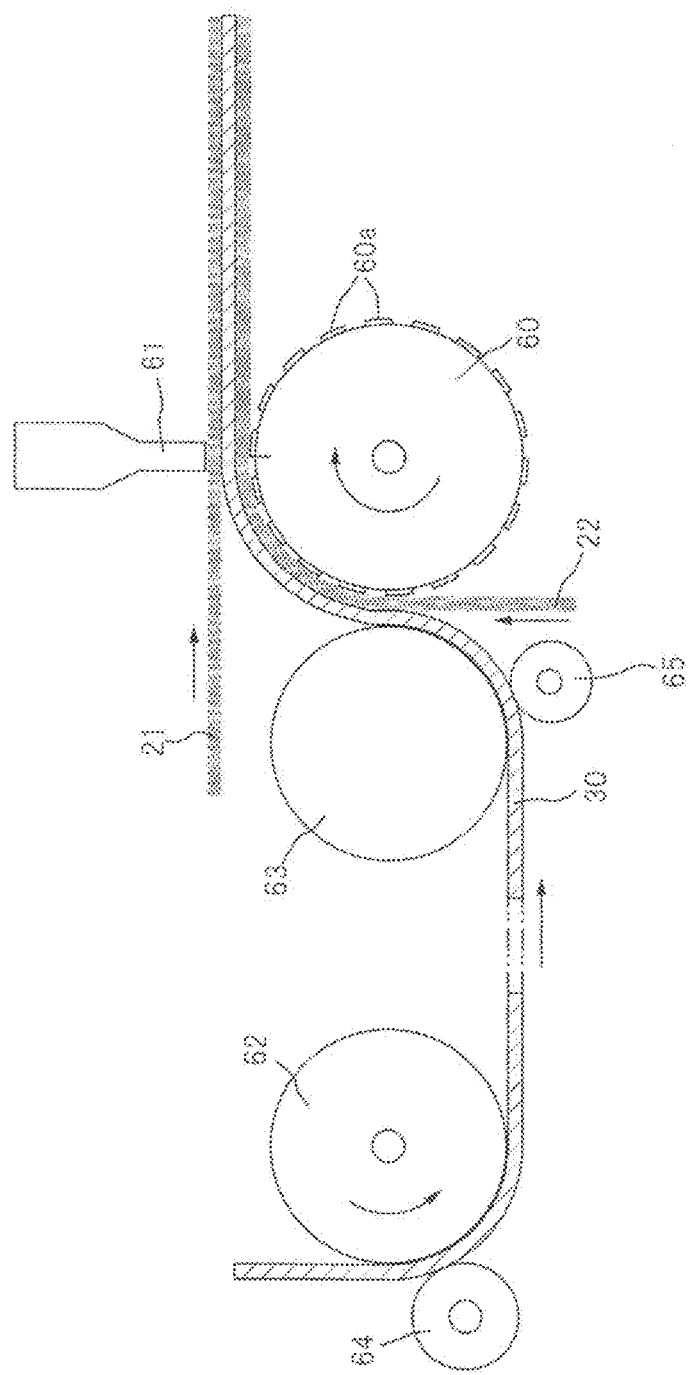
FIG. 12 is a schematic diagram of a fourth bonding example according to the present invention.

As can be inferred from the result of FIG. 13, when stepwise stretching (elongation) is performed as in the example of FIG. 12, in comparison with one stage stretching (elongation) as in the first bonding example to the third bonding example, the separation distance from the nip position to the bonding position becomes longer, which is not preferable. One stage stretching (elongation) as in the first bonding example to the third bonding example is desirable, and it is desirable that the elastic film does not stretch on the upstream side of the nip position.

Figure 14:
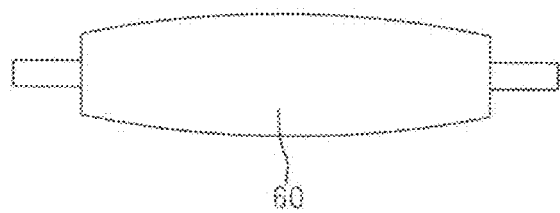
FIG. 14 is a diagram for explaining a crown roll.

It is preferable that the anvil roll 60 is a crown roll as illustrated in FIG. 14. The length of the anvil roll 60 is preferably about 1000 mm.

The amount of crown can be selected appropriately, but if necessary, the amount of crown can be adjusted by cooling the end of the roll.

On the other hand, the protrusions 60a of the anvil roll 60 can be formed so as to be denser toward the center of the roll length. In such arrangement, the central portion is most thermally expanded, and the crown is easily applied.

On the other hand, it is preferable to use die steel for the material of the anvil roll 60, and the optimal hardness is HRC 60 to 61.

Figure 6:
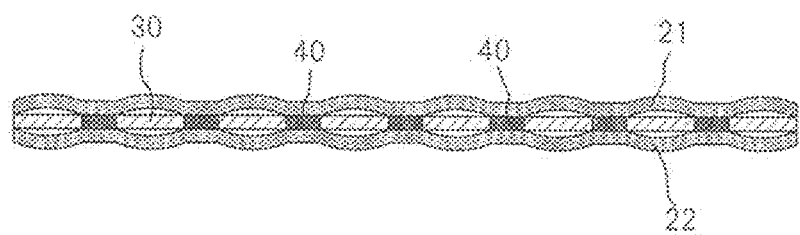
FIG. 6 is a cross-sectional view for explaining the stretchable sheet in a state where it is bonded.
Figure 7:
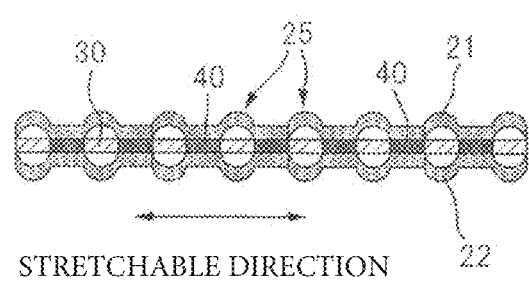
FIG. 7 is a cross-sectional view for explaining the stretchable sheet in a state where it is contracted.

FIG. 6 schematically illustrates a section of the stretchable sheet after bonding in a stretched state (however, a through hole is not yet formed). When the stretched state of the stretchable sheet in the MD (the right-left direction in FIG. 7) is released, as illustrated in FIG. 7 (schematic view), the stretchable sheet contracts due to the contracting force of the elastic film 30 and can be stretched by applying an external force. Therefore, if the stretchable sheet is applied for example to a disposable diaper, when the stretchable direction of the stretchable sheet is made to coincide with the front-back direction of the disposable diaper, the disposable diaper can be stretched in the front-back direction. When the stretchable direction is made to coincide with the width direction of the disposable diaper, the disposable diaper can be stretched in the circumferential direction of the lower torso part or the circumferential direction of the waist portion.

The stretchable sheet can be manufactured in the product production line, and the stretchable sheet obtained after cutting the web into a desired area after manufacturing the stretchable sheet web, can be applied to a predetermined site of a product.

In a conventional disposable diaper, it is common to fix a plurality of rubber threads in parallel on a sheet, but this causes inferior quality due to deterioration of a hot melt adhesive for fixing the rubber threads to the sheet, and it is difficult to keep stable productivity at the time of production. These problems can be solved by the above-described stretchable sheet.

In addition, as can be seen from the contracted state of FIG. 7, since, on the outer surface of the stretchable sheet, fine wrinkles or fine pleats are regularly generated, and texture of the sheet to the wearer's skin is improved.

On the other hand, in the above example, the first sheet layer 21 and the second sheet layer 22 are bonded by melting the elastic film 30. In this case, there are (1) a mode in which the first sheet layer 21 or the second sheet layer 22 is bonded on the surface of the elastic film 30, (2) a mode in which the surface portion of the elastic film 30 melts and it intrudes into fibers of each of the first sheet layer 21 and the second sheet 22 for bonding the sheet layers 21, 22, and (3) a mode in which almost all of the elastic film 30 melts, and it intrudes into fibers of each of the first sheet layer 21 and the second sheet layer 22 for bonding the sheet layers 21, 22. In the present invention, the bonding modes of the layers are not limited to these examples.

In the mode (3) among these modes, it can be evaluated that the first sheet layer 21 and the second sheet layer 22 are bonded directly, that is, while the elastic film is not remained.

In the above modes (1) to (3), the melting point of the elastic film 30 is lower than the melting points of the first sheet layer 21 and the second sheet layer 22. However, when the melting point of the elastic film 30 may be higher than the melting point of the first sheet layer 21 and/or the second sheet layer 22. In this case, the surface portion of the first sheet layer 21 and/or the second sheet layer 22 on the elastic film 30 side is activated or melted to be bonded to the elastic film 30.

Further, in addition to melting a part of the elastic film 30, the first sheet layer 21 and/or the second sheet layer 22 may also be melted and bonded.

The first sheet layer 21 and/or the second sheet layer 22 may be a nonwoven fabric, and the fiber may have a core/sheath structure. In this case, for example, only the sheath component of the fiber melts and can contribute to bonding.

In the stretchable sheet of the present invention, the shape, size and arrangement of the bonded portions may be uniform, and also the rate of the total area occupied by the bonded portions included in the unit area of the region to the unit area, that is, the area rate of the bonded portions can be selected.

Figure 1:
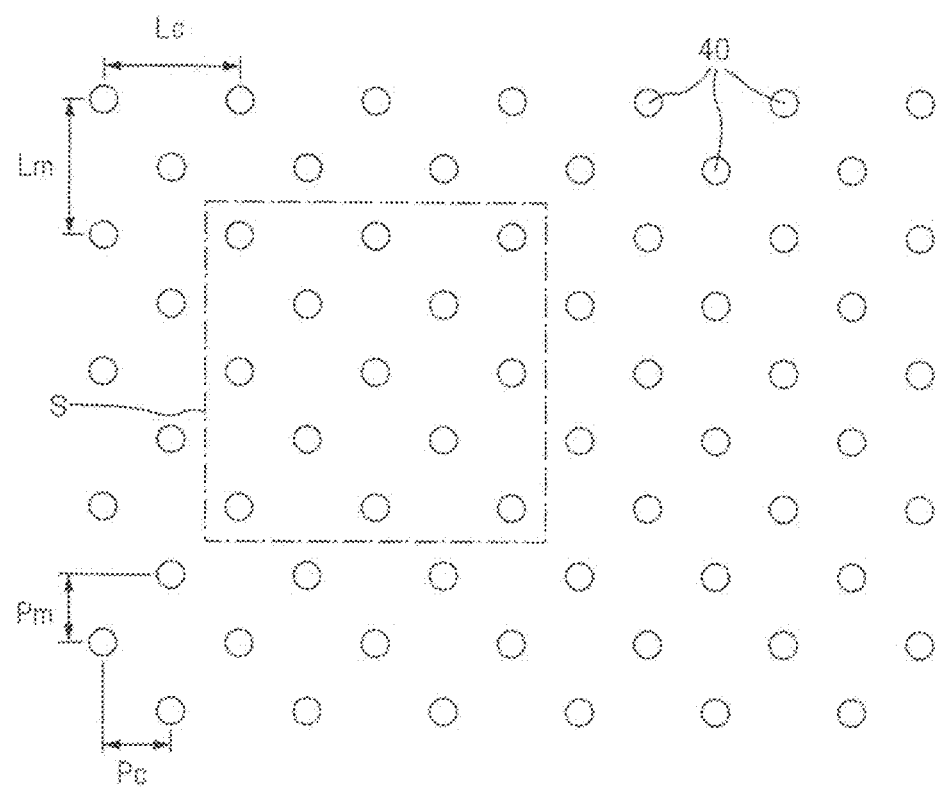
FIG. 1 is a plan view of an example of an arrangement pattern of bonded portions.

FIG. 1 is a plan view of an example in which an arrangement pattern of bonded portions (approximate to an arrangement pattern of a group of protrusions when an anvil roll is viewed in an unfolded state) is illustrated.

As in FIG. 1, as the area rate of the bonded portions in a state where the stretchable sheet is stretched to the elastic limit in the stretchable direction, the area rate of the total area occupied by the bonded portions 40, 40 . . . included in the unit area S is indicated by percentage. In this case, it is desirable to set the unit area S to such a size that ten or more bonded portions are included (comparison of stretching stresses is difficult with a small number of bonded portions). In the example of FIG. 1, thirteen bonded portions are included. In addition to a square shape, the outer shape that defines the unit area S may be another shape such as a rectangle or a circle.

An example of the bonded portion 40 is a circular shape illustrated in FIG. 1. It is obvious that the bonded portion 40 has a shape such as an ellipse or a rectangle. Lm in FIG. 1 is an arrangement interval length in the MD, Lc is an arrangement interval length in the orthogonal direction (cross direction: CD) orthogonal to the MD, Pm is a pitch length in the MD, and Pc is a pitch length of the orthogonal direction (CD).

FIGS. 2 to 6 illustrate embodiments in each of which the area rate of the bonded portions varies depending on the regions in the stretchable sheet.

Figure 2:
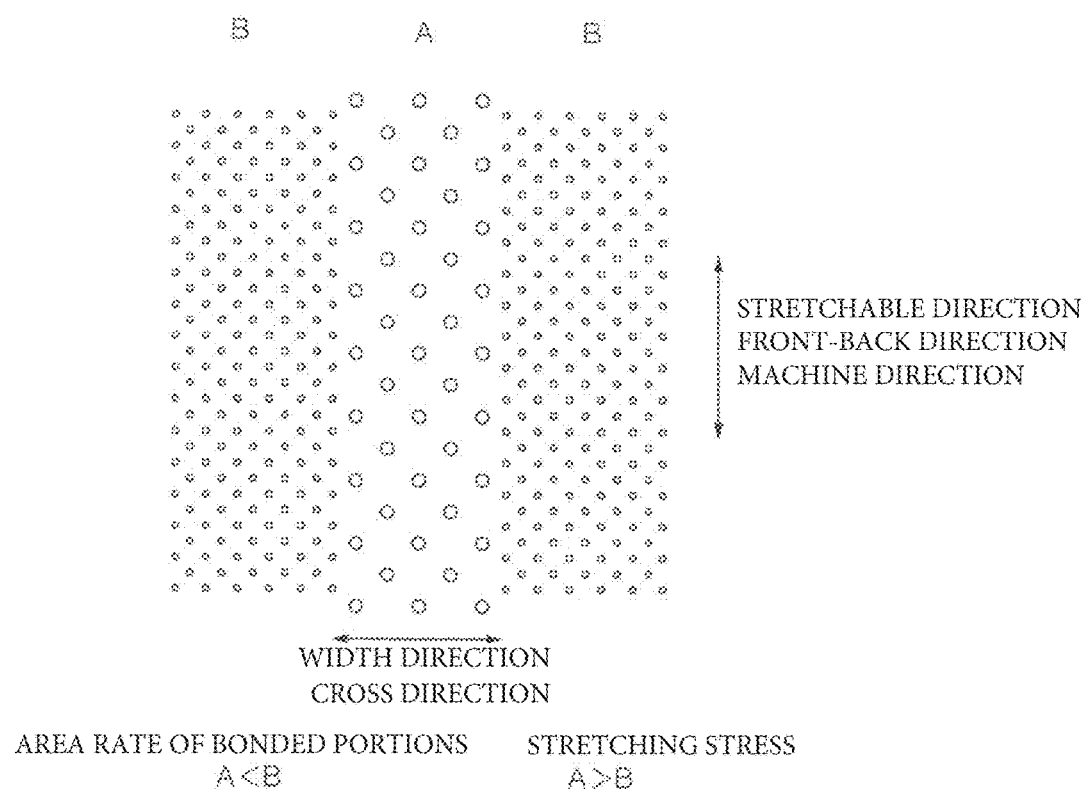
FIG. 2 is a schematic plan view of an example in which different area rates of the bonded portions are present.

FIG. 2 illustrates the relationship of the stretching stress between the regions A and B, which is set to be A>B by setting the relationship of the area rate of the bonded portions between the regions A and B to A<B For example, when the region A in which the pitch length Pm and the pitch length Pc are long is compared with the regions B in each of which the pitch length Pm and the pitch length Pc are short, the stretch rate is larger in the region A in which the pitch lengths Pm and Pc are long (that is, the area rate of the bonded portions is low) than in the regions B in each of which the pitch lengths Pm and Pc are short (that is, the area rate of the bonded portions is high). As a result, relationship of the stretching stress is set to A>B.

In the embodiment of FIG. 2, since the stretching stress in the lateral direction of FIG. 2 varies depending on the regions, the region A having a large stretching stress is made to correspond to the central section in the width direction of an absorbent article. Then, the regions B in each of which the stretching stress is small (that is, the stretchability is small) are made to correspond to both laterally external side sections with respect to the region A corresponding to the central section.

Figure 3:
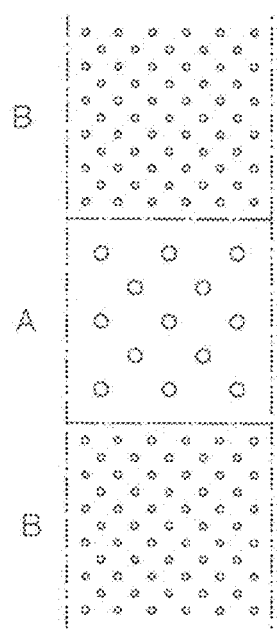
FIG. 3 is a schematic plan view of another example in which different area rates of the bonded portions are present.

In the case of FIG. 3, the regions B having small stretching stress are disposed on the front side and back side with respect to the region A at the middle in the front-back direction of a central part of the stretching sheet. In this example, the front and back regions B, B can correspond to, for example, the end portions in the front-back direction of a disposable diaper, and since the stretching stress is small at these end portions in the front-back direction, the shape stability is improved such that a wearer can easily wear the disposable diaper.

In the present invention, the difference in the area rate of the bonded portions can be obtained not only by varying the density of the bonded portions in an arrangement pattern but also by changing the area of each bonded portion.

Figure 4:
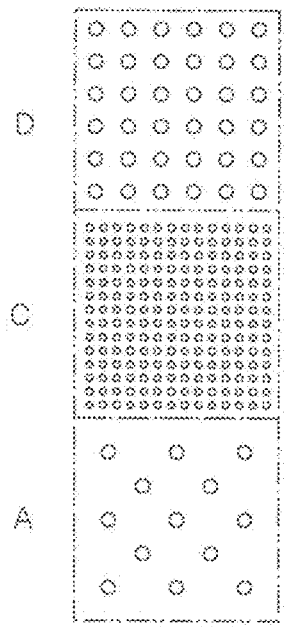
FIG. 4 is a schematic plan view of still another example in which different area rates of the bonded portions are present.
Figure 4:
Figure 5:
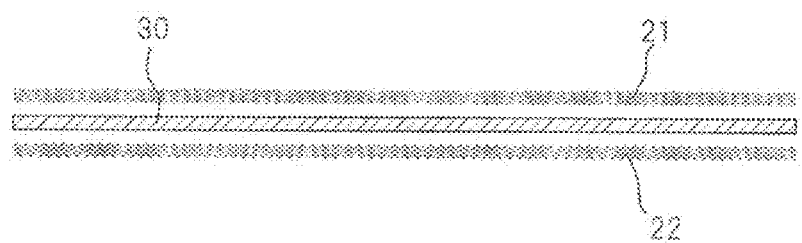
FIG. 5 is a cross-sectional view for explaining a stretchable sheet before bonded.

In order to make this easier to understand, FIG. 4 illustrates an example in which a large number of small bonded portions are disposed in the region C and the area occupied by the small bonded portions in the region C is the same as the area occupied by the bonded portions in the region D. By setting the relationship of the area of the bonded portions among the regions A, C and D to A<C=D, the relationship of the stretching stress is set to A>C=D.

Figure 8:
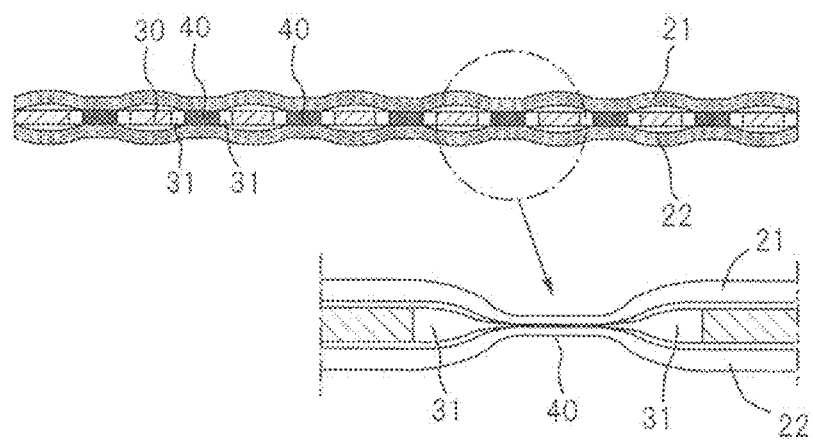
FIG. 8 is a cross-sectional view for explaining the bonded stretchable sheet in a state where through holes are formed.

Physical properties such as thickness, material, strain/stress characteristic, melting point and the like of the elastic film can be appropriately selected. By selecting the relationship among this elastic film, the ultrasonic melting energy applied to the elastic film, and the stretch rate of the elastic film at the time of manufacturing the stretchable sheet, as illustrated in FIG. 8, the through hole 31 can be formed around each of the bonded portions 40. When the first sheet layer 21 and the second sheet layer 22 are formed using, for example, nonwoven fabrics as the materials, since the nonwoven fabrics exhibit air permeability, air permeability is exhibited on the front surface and back surface of the stretchable sheet due to the formed through holes 31. Therefore, when the stretchable sheet is used as, for example, an external sheet or an outer sheet of a disposable diaper, the air permeability of the disposable diaper is improved.

Although the reason why such a ventilation through hole 31 is formed is not necessarily clear, since the elastic film 30 is melted with the ultrasonic melting energy and the bonded portions 40 are thinned by pressing from the protrusions 60a of the anvil roll 60, it is considered that, at this time, while the elastic film 30 is also thinned, the peripheral portion of the bonded portion 40 reaches the breaking strength, breakage is started by the stretching stress acting on the stretched elastic film 3, the elastic film 30 contracts to an equilibrium point, and the through hole 31 opens.

Figure 15:
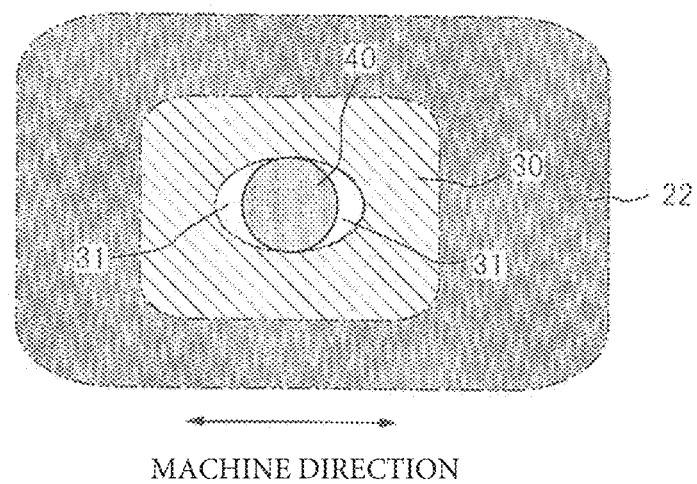
FIG. 15 is a plan view for explaining an example for forming a through hole.

FIG. 15 schematically illustrates an example of the through hole 31 formed for the bonded portion 40 which is formed in the case of the circular protrusion 60a. Substantially crescent shaped through holes 31 are formed on both sides in the MD (stretchable direction) of the bonded portion 40.

Figure 16:
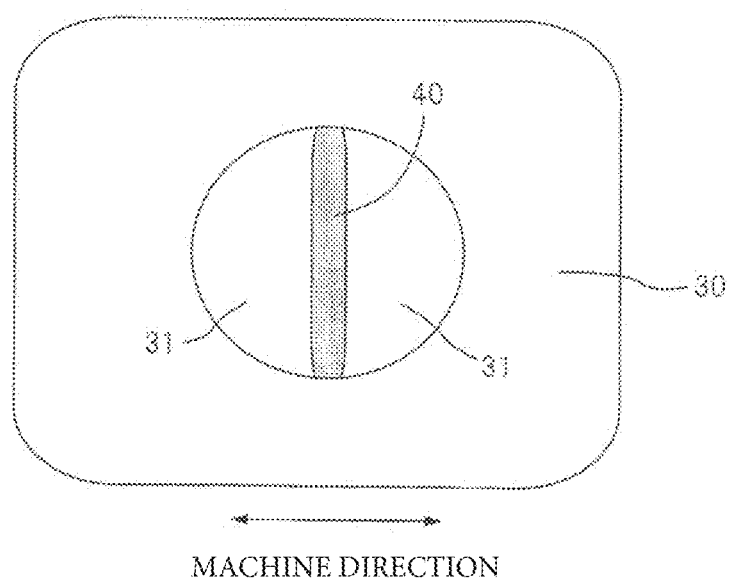
FIG. 16 is a plan view for explaining an example for forming a through hole in a different embodiment.

The bonded portion can be elongated in the direction (CD) orthogonal to the stretchable direction (MD). In this case, for example, as illustrated in FIG. 16, semicircular through holes 31 each having a large opening can be formed, which is a preferable means when it is desired to increase the air permeability.

On the other hand, it is not indispensable for the through hole 31 to be formed in all the bonded portions. If it is required to reliably form the through hole 31 or to make a large opening, the method indicated in FIG. 15 can be adopted.

Figure 17:
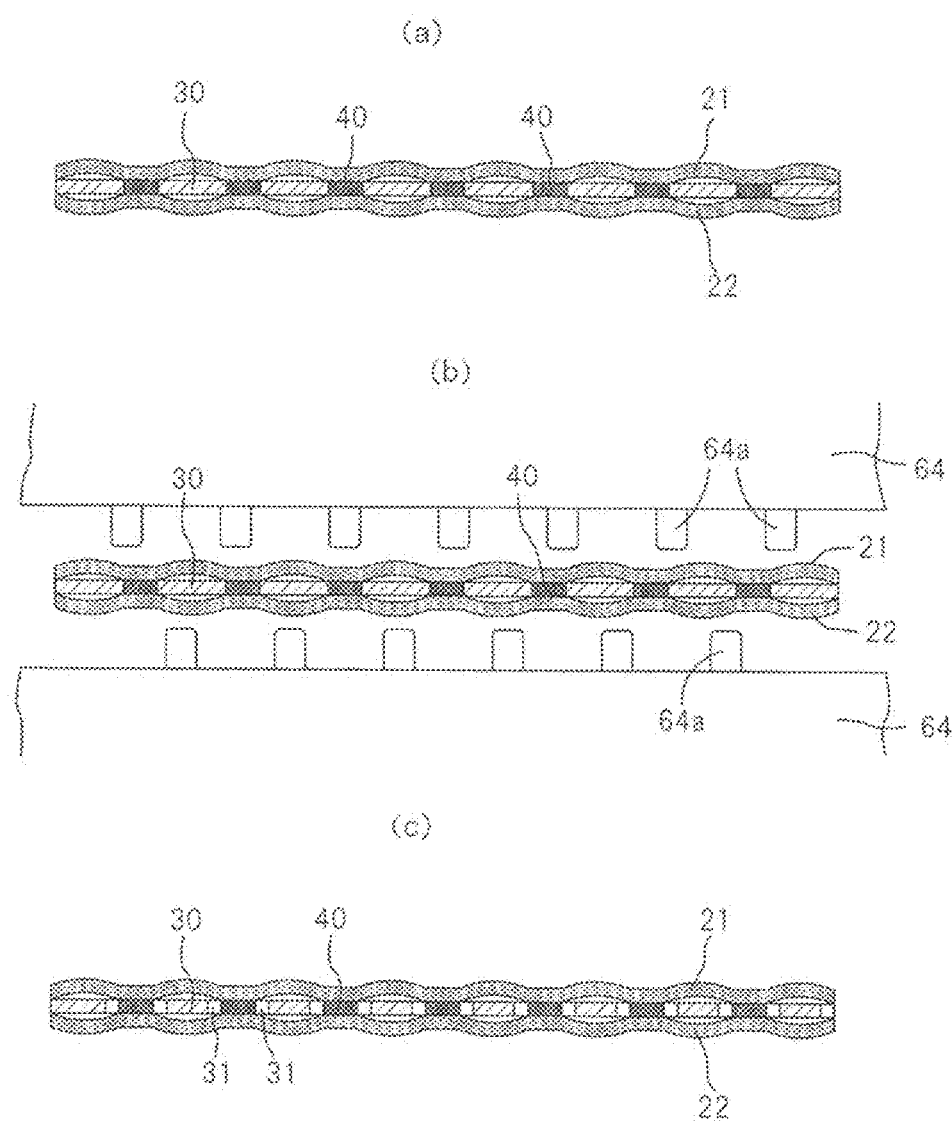
FIG. 17 is a cross-sectional view for explaining an example for forming compulsorily a through hole.

That is, as illustrated in FIG. 17(b), the stretchable sheet provided with the bonded portions 40 is passed between a pair of the rolls 64 having projections or protrusions 64a, each protrusion 64a of one roll 64 is inserted between each pair of adjacent protrusions 64a of the other roll 64, and a deforming force is applied to the stretchable sheet to form the through hole 31.

Meanwhile, the shapes of the individual bonded portions 40 and the through holes 31 in the natural length state can be arbitrary shapes such as polygonal shapes (including linear and rounded) such as a perfect circle, an elliptical shape, and a rectangular shape, a star shape, a cloud shape, and the like. The size of each bonded portion 40 may be determined appropriately, but if it is too large, the hardness of the bonded portion 40 exerts an influence on the texture, and if it is too small, a bonded area becomes too small and materials are insufficiently adhered. Therefore, in the usual case, the area of each bonded portion 40 is preferably about 0.14 to 3.5 $mm^2$. The area of an opening of each through hole 31 may be equal to or more than that of the bonded portion because the bonded portion is formed through the through hole 31, and it is preferable to set to about 1 to 1.5 times the area of the bonded portion.

Further, for the bonded portions of the present invention, a main elastic region may be directly transferred to a non-elastic region, but it is also possible to provide a transition elastic region between the main elastic region and the non-elastic region.

In general, the area and the area rate of the individual bonded portions 40 in each region are preferably set as follows.

(Non-Stretchable Region)

The area of the bonded portion 40: 0.14 $mm^2$ to 3.5 $mm^2$ (particularly 0.25 $mm^2$ to 1.0 $mm^2$)

The area rate of the bonded portions 40: 16% to 45% (especially 25% to 45%)

(Main Stretchable Region)

The area of the bonded portion 40: 0.14 $mm^2$ to 3.5 $mm^2$ (particularly 0.14 $mm^2$ to 1.0 $mm^2$)

The area rate of the bonded portions 40: 1.8% to 19.1% (particularly 1.8% to 10.6%)

(Transition Elastic Region)

The area of the bonded portion 40: 0.14 $mm^2$ to 3.5 $mm^2$ (particularly 0.25 $mm^2$ to 1.0 $mm^2$)

The area rate of the bonded portions 40: 8% to 22.5% (particularly 12.5% to 22.5%)

Figure 18:
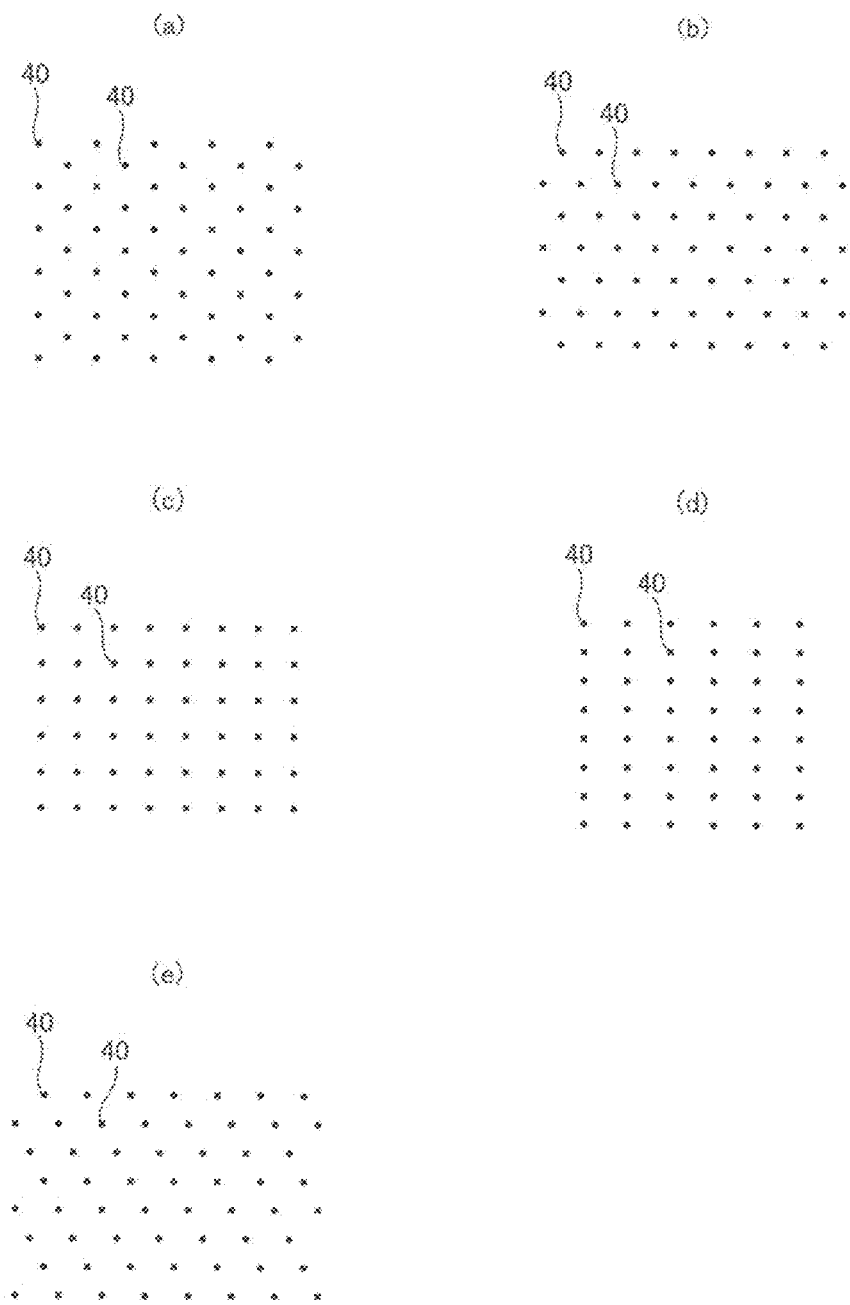
FIG. 18 is a plan view illustrating various arrangement examples of bonded portions.

Although the planar arrangement of the bonded portions 40 and the through holes 31 can be appropriately determined, it is preferable to adopt a planar arrangement in which they are regularly repeated, such as an oblique lattice shape as illustrated in FIG. 18(a), a hexagonal lattice shape (also referred to as a staggered shape) as illustrated in FIG. 18(b), a square lattice shape as illustrated in FIG. 18(c), a rectangular lattice shape as illustrated in FIG. 18(d), and a parallelotope lattice shape as illustrated in FIG. 18(e) (two groups are provided such that a large number of parallel oblique row groups cross each other in the drawing) (including those inclined at an angle of less than 90° with respect to the stretchable direction). Additionally, it is also possible to adopt a planar arrangement in which a group of the bonded portions 40 (each group may be regularly or irregularly arranged, and may be a pattern, a letter shape etc.) can be regularly repeated. The arrangement pattern of the bonded portions 40 and the through holes 31 may be the same in the main elastic region, the transition elastic region, and the non-stretchable region, or may be different.

The elastic film 30 is not particularly limited, and a resin film having elasticity can be used without particular limitation. A blend of one or two or more thermoplastic elastomers such as styrene elastomers, olefin elastomers, polyester elastomers, polyamide elastomers and polyurethane elastomers, which is processed into a film shape by extrusion molding such as T-die method or inflation method can be used. As the elastic film 30, besides a non-porous film, it is also possible to use a film having a large number of holes or slits for ventilation. In particular, it is preferable that in the elastic film 30, the tensile strength in the stretchable direction is 8 to 25 N/35 mm, the tensile strength in the direction orthogonal to the stretchable direction is 5 to 20 N/35 mm, the tensile elongation in the stretchable direction is 450 to 1050%, and the tensile elongation in the direction orthogonal to the stretchable direction is 450 to 1400%. Now that the tensile strength and the tensile elongation (tensile elongation at break) refer to values obtained by measuring at an initial chuck interval of 50 mm and a speed of testing of 300 mm/min according to JIS K7127: 1999 "Plastics—Determination of tensile properties—" except that the test piece is formed into a rectangular shape having a width of 35 mm×a length of 80 mm using a tensile tester (for example, AUTOGRAPHAGS-G100N manufactured by SHIMADZU Corporation). The thickness of the elastic film 30 is not particularly limited, but it is preferably about 20 to 40 μm.

Although the basis weight of the elastic film 30 is not particularly limited, it is preferably about 30 to 45 g/m², and particularly preferably about 30 to 35 g/m².

Explanation of Terms Used Herein

The following terms in the specification have the following meanings unless otherwise specified in the specification.

"Stretch rate" represents a value relative to the natural length (100%).

"Basis weight" is measured as follows. After the sample or test piece is preliminarily dried, it is allowed to stand in a test room or apparatus under normal conditions (the test location is at a temperature of 20±5° C. and with a relative humidity of 65% or less) until the constant mass. The preliminary drying is to make the sample or test piece be constant mass in an environment at a temperature not exceeding 50° C. within a relative humidity of 10 to 25%. The fibers of an official moisture regain of 0.0% does not need preliminary drying. A cut sample of dimensions of 200 mm×250 mm (±2 mm) is cut using a cutting template (200 mm×250 mm, ±2 mm) from a test piece in the constant mass. The sample is weighed, and the weight is multiplied by 20 into the weight per one square meter. The resulting value is defined as the basis weight.

In the absence of description about environmental conditions in a test room or apparatus under normal conditions (the test location is at a temperature of 20±5° C. and a relative humidity of 65% or less).

INDUSTRIAL APPLICABILITY

The stretchable sheet of the present invention can be used for all absorbent articles having a stretchable structure such as underpants-type disposable diapers, various types of disposable diapers such as tape type and pad type, sanitary napkins and the like.

Further, while bonding in the production line of absorbent articles is performed, the stretchable sheet according to the present invention can be manufactured as a sheet constituting, for example, the back surface of each absorbent article.

REFERENCE SIGNS LIST

A to D region
21 first sheet layer
22 second sheet layer
30 elastic film
31 through hole
40 bonded portion
60 anvil roll
61 ultrasonic horn
63 counter roll

The invention claimed is:

1. A method for manufacturing a stretchable sheet, comprising:
   a supplying step in which a stretchable elastic film is interposed in a stretched state between a first sheet layer having no elasticity and a second sheet layer having no elasticity; and
   a bonding step in which, in a state where the elastic film is interposed in a stretched state between the first sheet layer and the second sheet layer in the supplying step, the first sheet layer and the second sheet layer are bonded directly or via an elastic film at a plurality of bonded portions by applying heat melt energy to a region of the plurality of bonded portions spaced apart from each other by a heat melting apparatus from the outside of the first sheet layer and the second sheet layer to melt the elastic film;
   wherein the heat melting apparatus has an anvil roll and an ultrasonic horn, the anvil roll has a plurality of protrusions spaced apart from each other in a roll length direction and an outer circumference direction on an outer surface of the anvil roll such that bonding is performed by the ultrasonic horn and a group of the protrusions of the anvil roll at a bonding position;
   wherein a counter roll is disposed apart from the anvil roll, and the elastic film is not nipped between the anvil roll and the counter roll;
   wherein a nip roll that nips the elastic film is disposed corresponding to the counter roll, and
   the elastic film passes through a nip position between the counter roll and the nip roll, along the counter roll, and then along the anvil roll,
   wherein a circumferential speed of the anvil roll is faster than a circumferential speed of the counter roll and the nip roll to stretch the elastic film;
   wherein a holding angle α from the nip position to a position where the elastic film is separated from the counter roll is 300° to 30°, and a holding angle β from a position where the elastic film starts to be held by the anvil roll to the bonding position is 270° to 30°,
   wherein a distance between the nip position and the bonding position is less than 250 mm; and
   wherein a distance from a position where the elastic film is separated from the counter roll to the position where the elastic film starts to be held by the anvil roll is 50 mm or less.

2. The method for manufacturing a stretchable sheet according to claim 1, wherein the anvil roll is a crown roll.

3. The method for manufacturing a stretchable sheet according to claim 1, wherein the protrusions are disposed in a staggered shape.

4. The method for manufacturing a stretchable sheet according to claim 1, wherein, a hole is not formed in the entire of the region of the bonded portions and the first sheet layer and the second sheet layer are allowed to remain in the bonding step, and
   a through hole is formed at least in a boundary portion in the stretchable direction between the elastic film and the bonded portion.

5. The method for manufacturing a stretchable sheet according to claim 1, wherein:
   the elastic film is additionally nipped between a pre-roll and a pre-nip roll such that the elastic film is configured to pass through a nip position between the pre-roll and the pre-nip roll and then pass through the nip position between the counter roll and the nip roll; and
   wherein a circumferential speed of the pre-roll and the pre-nip roll, the circumferential speed of the counter roll and the nip roll, and the circumferential speed of the anvil roll are gradually increased.

* * * * *